United States Patent
Colston et al.

(10) Patent No.: US 7,122,195 B2
(45) Date of Patent: Oct. 17, 2006

(54) MUTANT MYCOBACTERIA FOR USE IN THERAPY

(75) Inventors: Jo Colston, deceased, late of Greater London (GB); by Kay Colston, legal representative, Surrey (GB); Eric Boettger, Zurich (CH); Peter Sander, Zurich (CH); Burkhard Springer, Zurich (CH)

(73) Assignee: Erik C. Boettger, Zurich (CH)

( * ) Notice: Subject to any disclaimer, the term of this patent is extended or adjusted under 35 U.S.C. 154(b) by 272 days.

(21) Appl. No.: 10/450,953

(22) PCT Filed: Dec. 18, 2001

(86) PCT No.: PCT/GB01/05617

§ 371 (c)(1),
(2), (4) Date: Oct. 15, 2003

(87) PCT Pub. No.: WO02/50262

PCT Pub. Date: Jun. 27, 2002

(65) Prior Publication Data

US 2004/0057966 A1    Mar. 25, 2004

(30) Foreign Application Priority Data

Dec. 18, 2000  (GB) .................. 0030857.7

(51) Int. Cl.
*A61K 39/04* (2006.01)
*A61K 49/00* (2006.01)
*A01N 63/00* (2006.01)
*A01N 48/00* (2006.01)

(52) U.S. Cl. .............. 424/248.1; 424/9.1; 424/9.2; 424/93.1; 424/93.2; 435/440; 435/471; 435/243; 435/253.1; 536/23.1; 536/23.7; 536/23.4; 536/24.32

(58) Field of Classification Search .............. 424/9.1, 424/9.2, 248.1, 93.1, 93.2; 435/440, 471, 435/243, 253.1; 536/23.1, 23.7, 23.4, 24.32
See application file for complete search history.

(56) References Cited

OTHER PUBLICATIONS

Kumar et al; "Functional Characterization of the Precursor and Spliced Forms of RecA Protein of Mycobacterium Tuberculosis"; Biochemistry, vol. 35, Feb. 13, 1996, pp. 1793-1802. XP00107081.

Papavinasasundarm et al; "Construction and Complementation of a recA Deletion Mutant of Mycobacterium Smegmatis Reveals That the Intein in Mycobacterium Tuberculosis recA Does Not Affect RecA Function"; Molecular Microbiology, vol. 30, No. 3, 1998, pp. 525-534, XP002201173.

Frischkorn et al; "Investigation of Mycobacterial recA Function: Protein Introns in the RecA of Pathogenic Mycobacteria do not Affect Competency For Homologous Recombination"; Molecular Microbiology, vol. 29, No. 5, 1998, pp. 1203-1214, XP000961254.

McFadden; "Recombination in Mycobacteria"; Molecular Microbiology, vol. 21, No. 2, 1996, pp. 205-211, XP001070919.

Sander et al; "Mycobacterium Bovis BCG recA Deletion Mutant Shows Increased Susceptibility to DNA-Damaging Agents But Wild-Type Survival N a Mouse Infection Model"; Infection and Immunity, vol. 69, No. 6, Jun. 2001, pp. 3562-3568, XP001070859.

*Primary Examiner*—Rodney P Swartz
(74) *Attorney, Agent, or Firm*—Nixon & Vanderhye P.C.

(57) ABSTRACT

This invention relates to recA mutant mycobacteria, particularly mutants of mycobacterial species which are members of the *Mycobacterium tuberculosis* complex, such as *M. bovis* BCG and *M. tuberculosis*. These mutant mycobacteria are useful as immunotherapteutic agents and vaccines for the treatment of a range of disorders, including tuberculosis.

14 Claims, 6 Drawing Sheets

MUTANT MYCOBACTERIA FOR USE IN THERAPY

Figure 1:
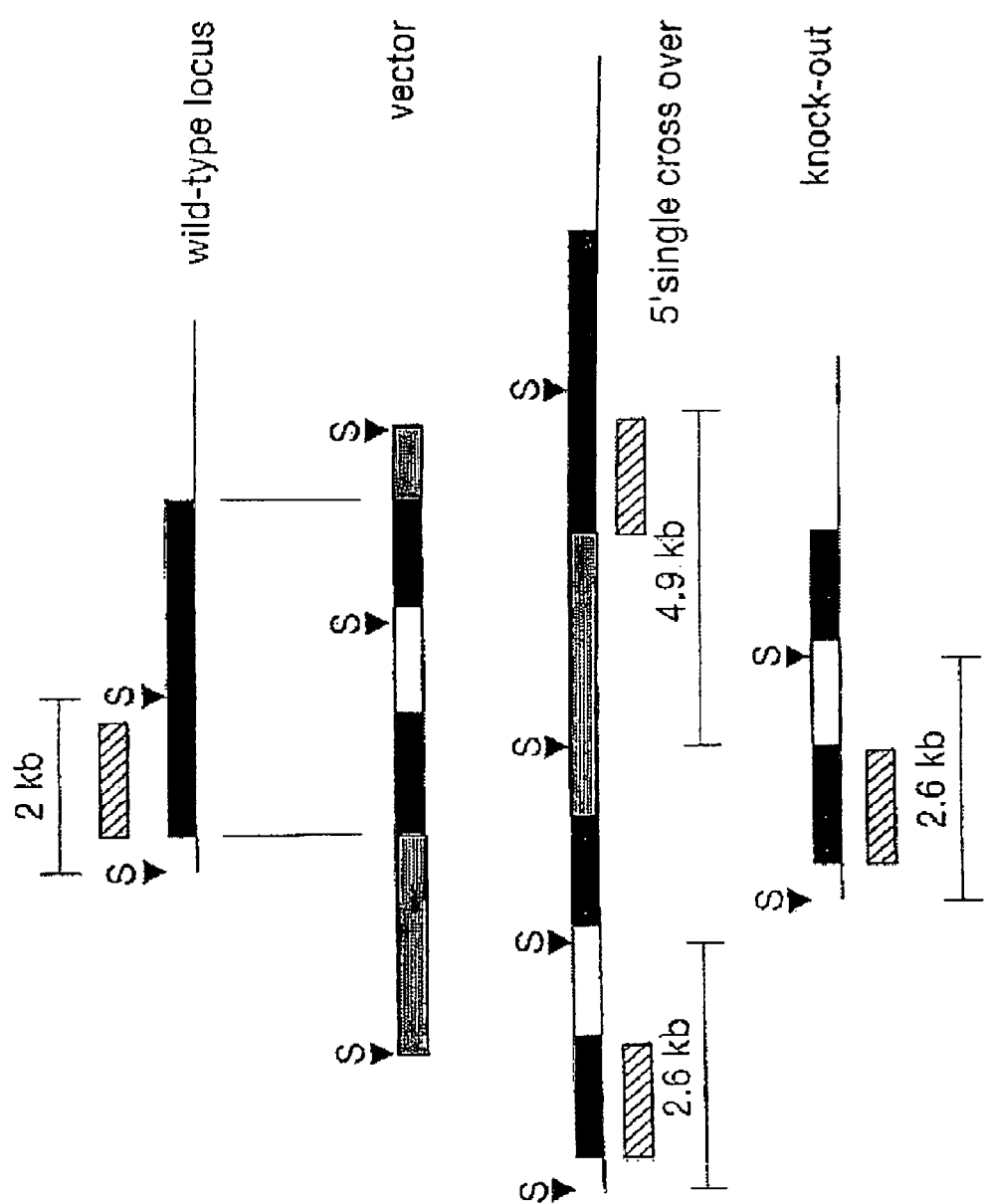

This application is the US national phase of international application PCT/GB01/05617 filed 18 Dec. 2001, which designated the US, and claims priority from GB 0030857.7 filed 18 Dec. 2000. The entire contents of these applications are incorporated herein by reference.

This invention relates to *Mycobacterium* mutants, particularly mutants of mycobacterial species which are members of the *Mycobacterium tuberculosis* complex, such as *M.bovis* BCG and *M. tuberculosis*, which are useful as immunotherapeutic agents, vaccines, or carriers for use in generating new vaccines. Such agents are useful in the treatment of a range of disorders, including tuberculosis.

Infection with *M. tuberculosis* is a major cause of human morbidity and mortality. Despite many efforts in mycobacterial genetics little is known about its virulence factors and mechanisms of pathogenicity.

*Mycobacterium bovis* BCG is a member of the *M. tuberculosis* complex which is used as live vaccine against *M. tuberculosis* infection and has been administered to more than a billion people world-wide (Cohn, D. L. (1997) *Am. J. Med. Sci.* 6: 372–376, Cohn, M. L. et al (1954) *Am. Rev. Tuberc*. 70: 641–664). BCG has also been used as a non-specific immunotherapeutic agent in cancer treatment (Nseyo, U. O., and Lamm, D. L. (1997) *Semin. Surg. Oncol.* 13: 342–349; Patard, J. J. et al (1998). *Urol. Res.* 26: 155–159). Non-virulent strains of *M. tuberculosis* have also developed for use as vaccines.

BCG has a chequered history in efficacy trials. Protection ranges between 0 and 70% and BCG shows a great deal of geographic variability in its ability to protect against lung tuberculosis (Fine, P. E. M. (1988) *British Medical Bulletin* 44: 704–716). However, in most published trials, BCG has revealed significant protection against early childhood tuberculosis and disseminated manifestations of the disease (Cohn, 1997 supra).

There are several possible reasons for this variability in efficacy, including genetic differences in the host, different exposure of host to environmental non-tuberculous mycobacteria and genetic variability in BCG daughter strains.

A variety of genetic differences have been shown between daughter strains of BCG, including point mutations (Behr et al; J. Bacteriol. 2000 182:3394), variable RFLP (Behr and Small Vaccine 1999 17:915), direct repeat patterns (Howard et al J. Clin. Microbiol. 1997 35:965), variable intergenic repeats (Frothingham et al Microbiol. 1998 144:1189) and gene deletions (Behr et al (1999) Science 284: 1520–153). The mechanisms and genes responsible for genetic instability in BCG have not been characterised. Genetic instability may be a cause of variability in the efficacy of BCG.

One of the many proteins known to be involved in DNA repair in prokaryotic and eukaryotic cells is recA, which regulates the error-prone DNA repair mechanism (SOS response) and is a key element of homologous recombination (Walker, G. C. (1995) *Trends Biol. Sci.* 20: 416–420). The RecA of the *Mycobacterium tuberculosis* complex is known to have an unusual structure, in that it contains a protein splicing element, termed intein (Davis, E. O. et al (1991) *J. Bacteriol*. 173: 5653–5662). Difficulties in achieving homologous recombination in *M. tuberculosis* complex have been attributed to this unusual structure, which may inhibit the activity of the protein, (McFadden, J. (1996) *Mol. Microbiol*. 21: 205–211) although other data suggests that the *M. tuberculosis* RecA intein does not interfere with RecA function (Frischkorn, K. et al (1998) *Mol. Microbiol*. 29: 1203–1214; Papavinasasundaram, K. G. et al (1998) *Mol. Microbiol*. 30: 525–534).

Members of the *M. tuberculosis* complex, such as *M. bovis* BCG and *M. tuberculosis* are invasive micro-organisms which infect mammalian hosts. Phagocytic cells in a mammalian host are able to generate various chemical species including superoxide, hydrogen peroxide, and other reactive oxygen metabolites which damage microbial DNA, proteins, and membranes and present a hostile environment to invasive microorganisms (Hassett, D. J., and Cohen, M. S. (1989) *FASEB J*. 3: 2574–2582). Microorganisms possess various mechanisms to cope with the oxidative stress induced by phagocytes, including the recA dependent DNA repair system which repairs any damage resulting from this oxidative stress (Storz, G. et al (1990) *Trends Genet*. 6: 363–368). Such mechanisms are particularly important for the survival of intracellular pathogens in the body DNA repair mechanisms in general and RecA function in particular have been shown to be essential for survival of intracellular pathogens by repairing DNA damage resulting from oxidative stress arising from the cellular environment e.g. in *Salmonella typhimurium* (Buchmeier, N. A., et al (1995) *J. Clin. Invest*. 95: 1047–1053). This is supported by evidence from *E. coli* showing that resistance to $H_2O_2$ correlates with the recA genotype, rather than with levels of catalase, peroxidase or superoxide dismutase (Carlsson J. and Carpenter V. (1980) 142: 319–321) and from *Erwinia carotovora*, in which the RecA-dependent SOS induction has been shown to enhance virulence (McEvoy et al (1990) J. Bacteriol. 172: 3284–3289).

RecA has also been generally considered to play a role in the virulence of mycobacteria, particularly intracellular pathogens such as *M. tuberculosis* (Davis, E. O. et al (1991) *J. Bacteriol*. 173: 5653–5662), *M. bovis* BCG and other members of the *M. tuberculosis* complex.

Despite its widespread use, BCG is known to cause severe infections in immunocompromised individuals (Steg, A. et al (1989) *Eur. Urol*. 16: 161–164; Stone, M. M. et al (1995) *N. Engl. J. Med*. 333: 561–563; Hill, A. V. (1998) *Annu. Rev. Immunol*. 16: 593–617; Vesterhus, P. et al (1998) *Clin. Infect. Dis*. 27: 822–825). This indicates that this organism is endowed with residual virulence properties which may manifest in the absence of an effective immune response.

The ability of BCG to survive for prolonged periods without causing progressive infection in immunocompetent individuals is an important component of its protective properties (Bloom, B. R., and Fine, P. E. M.: Bloom, B. R. (ed.) Tuberculosis: pathogenesis, protection and control. ASM Press, New York, 1994 p: 531–558, Behr et al (1999) supra) and in animal models, the persistence of BCG correlates with protective efficacy. It is therefore important that any *M. bovis* BCG strain used in therapeutic applications is able to survive in an immunized immunocompetent host without causing disease.

Non-virulent strains of *M. tuberculosis* may also survive for prolonged periods without causing progressive infection in immunocompetent individuals and may be used in therapeutic applications. These strains are commonly generated by the inactivation of genes responsible for virulence. The protective efficacy of these strains is also correlated with persistence in an immunized individual.

*M. bovis* BCG has also been proposed as an ideal delivery system for expression of foreign antigens because of this long persistence in the immunized host (Matsuo, K. et al (1990) *Infect. Immun*. 58: 4049–4054; Winter, N. et al (1991) *Gene* 109: 47–54; Stover, C. K. et al (1991) *Nature*

351: 456–460; Aldovini, A., and Young, R. A. (1991) *Nature* 351: 479–482; Haeseleer, F. et al (1993) *Mol. Biochem. Parasit.* 57: 117–126; Hess, J., and Kaufmann, S. H. (1999) *FEMS Immunol. Med. Microbiol* 23: 165–173).

*M. bovis* BCG and *M. tuberculosis* are slow-growing, have low transformation efficiencies and are subject to non-homologous genetic rearrangements. The problems posed by the genetic manipulation of these organisms have hindered the development of improved recombinant strains.

The present inventors have developed a novel procedure for the generation of knock-out mutations in members of the *M. tuberculosis* complex such *M. bovis* BCG and *M. tuberculosis*, which is described herein. This has led to the unexpected discovery that, in contrast to other intracellular pathogens, the inactivation of RecA does not affect the persistence or virulence of mycobacteria of the *M. tuberculosis* complex within a host. Furthermore, such inactivation leads to improvements in the genetic stability of these mycobacteria.

The term '*M. tuberculosis* complex cell' as used herein refers to a cell of a mycobacterial species or strain which is a member of the *M. tuberculosis* complex. Mycobacteria which are members of the *M. tuberculosis* complex include *M. tuberculosis*, BCG, *M. bovis, M. africanum, M. canetti* and *M. microti.*

Mycobacteria of the *M. tubercolosis* complex have endogenous antigens which are cross-reactive with *M. tuberculosis*. Antibodies raised against such a cross-reactive antigen will also bind specifically to one or more antigens from *M. tuberculosis*. These cross-reactive antigens are able to evoke and/or potentiate an immune response against *M. tubercolosis* in an individual. Inoculation of an individual with a mycobacterium of the *M. tuberculosis* complex, or one or more antigens therefrom, primes the immune system to react against challenge with *M. tuberculosis* and may therefore potentiate an immune response against subsequent *M. tuberaculosis* infection. This may reduce or abolish the symptoms and/or duration of infection and thereby provide a protective effect against such infection.

A first aspect of the present invention provides a cell of a mycobacterium which is a member of the *M. tuberculosis* complex and which has an inactivated recA function.

A cell may be in an isolated and/or purified form, i.e. separated from substances present in its natural environment, such as constituents of a culture medium.

RecA function may be reduced or, more preferably, fully inactivated in cells and compositions of the present invention.

A mycobacterial cell of the present invention persists in a host immunized therewith. The presence of the recA mutation does not affect the ability of the cell to survive in the host and the cell is able to persist in tissue without causing progressive infection in an immunocompetent host.

Preferably, a *M. tuberculosis* complex cell, particularly a *M. tuberculosis* cell, according to the present invention is non-virulent (i.e. the genes responsible for virulence have been inactivated) and does not evoke disease symptoms in an individual. Such a cell may be used in pharmaceutical compositions and vaccines as described herein.

An *M. tuberculosis* complex cell of the present invention may be used in a range of therapeutic, prophylactic or other medical or veterinary applications.

RecA function in a *M. tuberculosis* complex cell may be inactivated by the inactivation of the recA gene. The recA gene may be inactivated by a mutation such as an insertion, deletion or frameshift mutation. Any mutation which inactivates or reduces the activity of the recA gene may be employed in accordance with the present invention. Mutations may occur in the coding region and affect (i.e. reduce or abolish) the recA activity of the expressed protein or in the non-coding region and affect (i.e. reduce or abolish) the expression of active recA protein.

Mutations may be induced in the recA gene of a cell by any one of a range of conventional techniques of genetic manipulation i.e. recombinant techniques, to produce a non-naturally occurring genetic sequence. Mutations may, for example, be carried out by replacing the endogenous recA gene of an *M. tuberculosis* complex cell, such as *Mycobacterium bovis* BCG or *Mycobacterium tuberculosis*, with a recA transgene which carries a mutation which reduces or inactivates the function of the recA transgene.

A mutation which reduces or inactivates the function of the recA transgene may comprise the replacement of recA sequence in a mutant recA gene with non-recA sequence. Non-recA sequence may include a gene encoding a positive selectable marker. Other suitable mutations are well known to those skilled in the art. A suitable recA transgene may thus comprise exogenous of non-natural nucleic acid sequence i.e. sequence not found in the recA gene of a wild-type mycobacterial cell.

The endogenous gene may be replaced by a transgene using homologous recombination, for example, using a method wherein the cell is transformed with a vector comprising a transgene, a positive selectable marker and a counterselectable marker. The transgene may comprise a gene encoding a positive selectable marker.

Screening for recA mutants is preferably carried out using a two stage selection. In a first stage, transformed cells in which the vector has integrated into the genome are identified by selecting for a positive marker on the vector. In a second stage, transformants are then isolated in which double cross over recombination, and therefore allelic replacement, has occurred. The present invention encompasses host cells which are members of the *M. tuberculosis* complex and which comprise such a vector.

Suitable dominant negative selectable markers include rpsL and SacB, which is preferably used in conjunction with an additional counterselectable marker, such as a thermosensitive origin of replication.

Other suitable methods for producing a mutant mycobacterial cell are described in Glickman. M. et al (2000) *Molecular Cell*. 5: 717–727.

A cell of a mycobacterium of the *M. tuberculosis* complex as described herein, for example a *Mycobacterium bovis* BCG or *Mycobacterium tuberculosis* cell, may be used in a method of treatment of the human or animal body, for example a method of therapeutic treatment.

A *M. tuberculosis* complex cell of the present invention may further comprise a gene encoding a polypeptide which is a non-mycobacterial or foreign antigen. Expression of such an antigen in an *M. tuberculosis* complex cell, for example, an *M. bovis* BCG cell allows the generation of an immune response in a vaccinated individual against the non-mycobacterial antigen. The cell may therefore be used as an antigen delivery system in the treatment of any disease, such as a pathogenic infection, which is ameliorated by an immune response against a particular antigen.

The improved genetic stability of mycobacterial cells of the present invention provides for the improved retention of the non-mycobacterial gene and therefore a more effective immune response.

Suitable antigens include viral, protozoal, tumour cell, bacterial and fungal antigens. For example, an antigen from *H. pylori*, Measles virus (Fennelly G. J. et al (1995) *J. Infect.*

*Dis.* 172: 698–705), Mumps virus, Rubeola virus (e.g. OspA: Stover, C. K. et al (1993) *J. Exp. Med.* 178: 197–209), *B. burgdorferi* (e.g. protein A: Langermann et al (1994) *Nature* 372: 552–555), Herpesvirus, Papillomavirus, Tetanustoxin, Diphtheriatoxin, *Pneumococcus* spp (e.g. Surface protein A: Langermann et al (1994) *J. Exp. Med.* 180: 2277–2286) tumour cells, Leishmania (e.g. surface proteinase gp63: Connell N. et al (1993) *Proc. Natl. Acad. Sci. USA.* 90: 11473–11477) or HIV (or SIV: Yasutomi Y. et al (1993) *J. Immunol.* 150: 3101–3107) may be used. Such an antigen may be useful in the treatment of ulcers, measles, mumps, rubeola, Lyme disease, herpes, cancer, tetanus, diphtheria, cancer, Leishmaniasis or AIDS respectively.

A further aspect of the present invention therefore provides a *M. tuberculosis* complex cell as described herein which comprises genetic material encoding an antigen or immunogen exogenous or foreign to the mycobacterium. Examples of a non-mycobacterial antigen or immunogen that may be encoded are listed above.

The *M. tuberculosis* complex cell is able to express the said genetic material upon infection of a host cell, thereby producing the encoded antigen or immunogen, to which an immune response may be generated.

An *M. tuberculosis* complex cell of the present invention may thereby confer immunity against a pathogen exogenous to the mycobacterium in a susceptible species immunised therewith.

Genetic material i.e. nucleic acid encoding an antigen or immunogen exogenous or foreign to the mycobacterium may be introduced using techniques described herein or other suitable techniques which are known in the art (Matsuo, K. et al (1990) *Infect. Immun.* 58: 4049–4054; Winter, N. et al (1991) *Gene* 109: 47–54; Stover, C. K. et al (1991) *Nature* 351: 456–460; Aldovini, A., and Young, R. A. (1991) *Nature* 351: 479–482; Haeseleer, F. et al (1993) *Mol. Biochem. Parasit.* 57: 117–126; Hess, J., and Kaufmann, S. H. (1999) *FEMS Immunol. Med. Microbiol* 23: 165–173).

A further aspect of the present invention provides the use of a nucleic acid comprising an inactivated recA transgene as disclosed herein for improving the genetic stability of a *M. tuberculosis* complex cell, without abolishing the virulence or persistence of the cell. In preferred embodiments, persistence is not affected.

The inactivated recA transgene may be used as described herein to replace the endogenous recA gene of the cell.

A further aspect of the present invention provides a method for improving the genetic stability of a *M. tuberculosis* complex cell without abolishing, preferably without affecting, the virulence or persistence of the cell, comprising inactivating a recA gene within the cell.

A related aspect of the present invention provides a method for improving the genetic stability of a vaccine comprising a *M. tuberculosis* complex cell without affecting the persistence of the cell in an individual, comprising inactivating a recA gene within the mycobacterial cell Inactivating a recA gene may comprise replacing an endogenous recA gene with an inactive recA transgene. The replacement may occur by homologous recombination as described herein.

A *M. tuberculosis* complex cell of the present invention may be manufactured and/or used in preparation, i.e. manufacture or formulation, of a composition such as a medicament, vaccine, pharmaceutical or veterinary composition or drug. These may be administered to individuals.

Individuals include humans and other mammals, including farm animals (e.g. cows) and wild animals (e.g. badgers) which are susceptible to infection with *Mycobacterium tuberculosis*.

Pharmaceutical or veterinary compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical or veterinary compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Another aspect of the present invention therefore provides a pharmaceutical or veterinary composition or vaccine comprising an *M. tuberculosis* complex cell and having an inactivated recA function as disclosed herein.

An inactivated recA function means an abolished or reduced recA activity within the cell. This may be achieved by inactivating an endogenous mycobacterial recA gene.

Such a pharmaceutical may be an immunotherapeutic agent, vaccine, or carrier of antigenic or immunogenic material and may be used to generate an immune response in the treatment of a disorder in an individual in which said response is beneficial. Suitable disorders include disorders in which an immune response against, for example, *M. bovis* BCG or *M. tuberculosis* is beneficial, for example, tuberculosis and cancer.

Another aspect of the present invention provides the use of a *M. tuberculosis* complex cell as described herein in the manufacture of a medicament for use in the treatment of a disorder in which an immune response against an antigen expressed by the *M. tuberculosis* complex cell is beneficial.

Such disorders include disorders in which an immune response against an endogenous *M. tuberculosis* cross-reactive antigen expressed by the mycobacterial cell is beneficial, for example, tuberculosis and cancer, and disorders in which an immune response against a foreign (non-tuberculosis, or non-mycobacterial) antigen expressed by a BCG cell is beneficial (for example, ulcers, measles, mumps, rubeola, Lyme disease, herpes, cancer, tetanus, diphtheria, cancer and AIDS).

Another aspect of the present invention provides a method of making a pharmaceutical or veterinary composition comprising admixing such a substance with a pharmaceutically acceptable excipient, vehicle or carrier, and optionally other ingredients.

Another aspect of the present-invention also provides a method comprising the administration of a M. tuberculosis complex cell as described herein to a mammal in need thereof for use in the treatment of a disorder in which an immune response against the cell is beneficial. Such disorders include tuberculosis and cancer.

A M. tuberculosis complex cell as described herein may be used to present foreign antigens as disclosed herein and for the purpose of generating an immune response against the foreign antigen. Such a cell may be used in the treatment of disorders characterised by the presence of a foreign antigen in the body, for example, infection by a pathogen.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

M. bovis BCG administration is well established throughout the world as a prophylactic treatment for tuberculosis. A skilled person in the field is familiar with the protocols, formulations, dosages and clinical practice associated with the administration of M. bovis BCG. Such protocols, formulations, dosages and clinical practice are entirely suitable for use with pharmaceutical compositions and vaccines of the present invention.

A composition may be administered alone or in combination with other treatments, either simultaneously or sequentially dependent upon the condition to be treated.

Aspects of the present invention will now be illustrated with reference to the accompanying figures described already above and experimental exemplification, by way of example and not limitation. Further aspects and embodiments will be apparent to those of ordinary skill in the art. All documents mentioned in this specification are hereby incorporated herein by reference.

FIG. 1 shows a schematic drawing of the BCG recA locus: the wildtype locus is shown along with the vector used for inactivation, a 5' single cross-over transformant and a knock-out mutant. black box: cloned recA fragment; thin black line: flanking genomic DNA; open box: aph-cassette; grey box: vector backbone; hatched box: probe used for Southern blot analysis; arrow heads and S: SmaI recognition sites.

Figure 2:
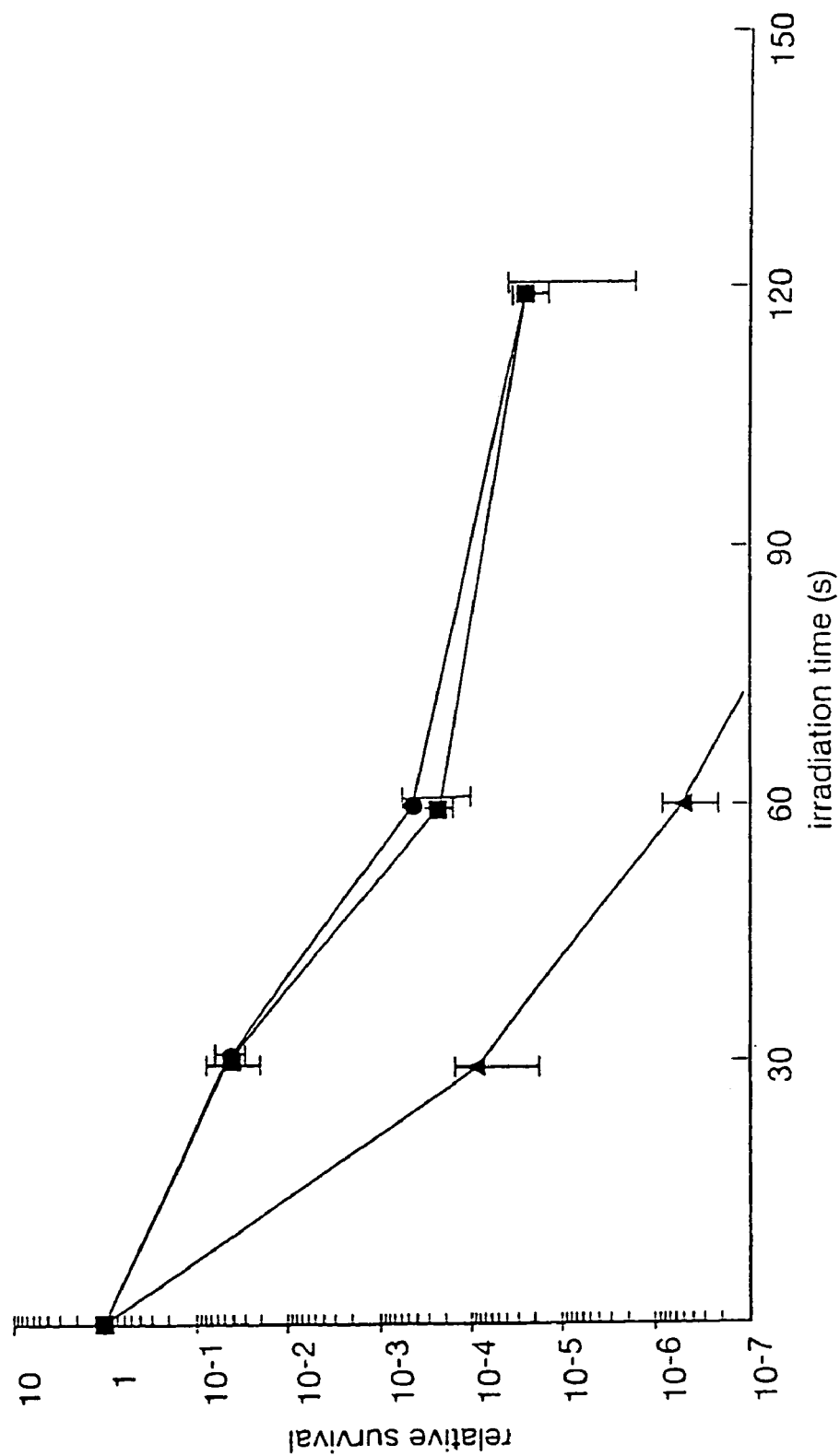

FIG. 2 shows the survival after UV irradiation. Parental M. bovis BCG (●), recA single cross-over transformant (■) and recA knock-out mutant (▲) were irradiated with UV light for the indicated times. Following irradiation the number of viable cells were determined by plating.

Figure 3:
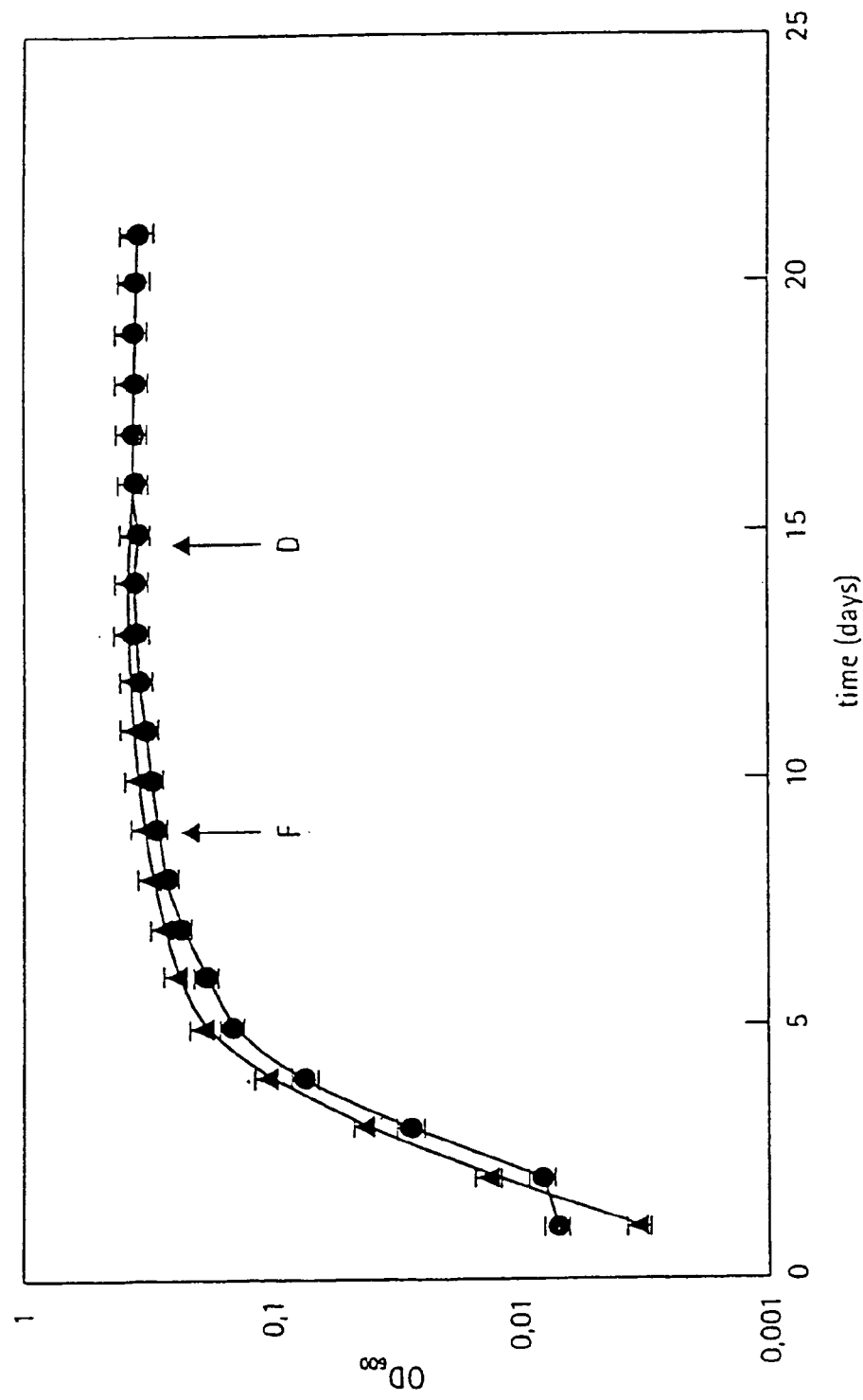

FIG. 3 shows growth under dormancy conditions. Parental M. bovis BCG (●)and the recA knock-out mutant(▲) were grown under dormancy culture conditions. Growth was determined by measuring the optical density. F and D indicate fading and complete decolorization of the methylene blue indicator, respectively.

Figure 4:
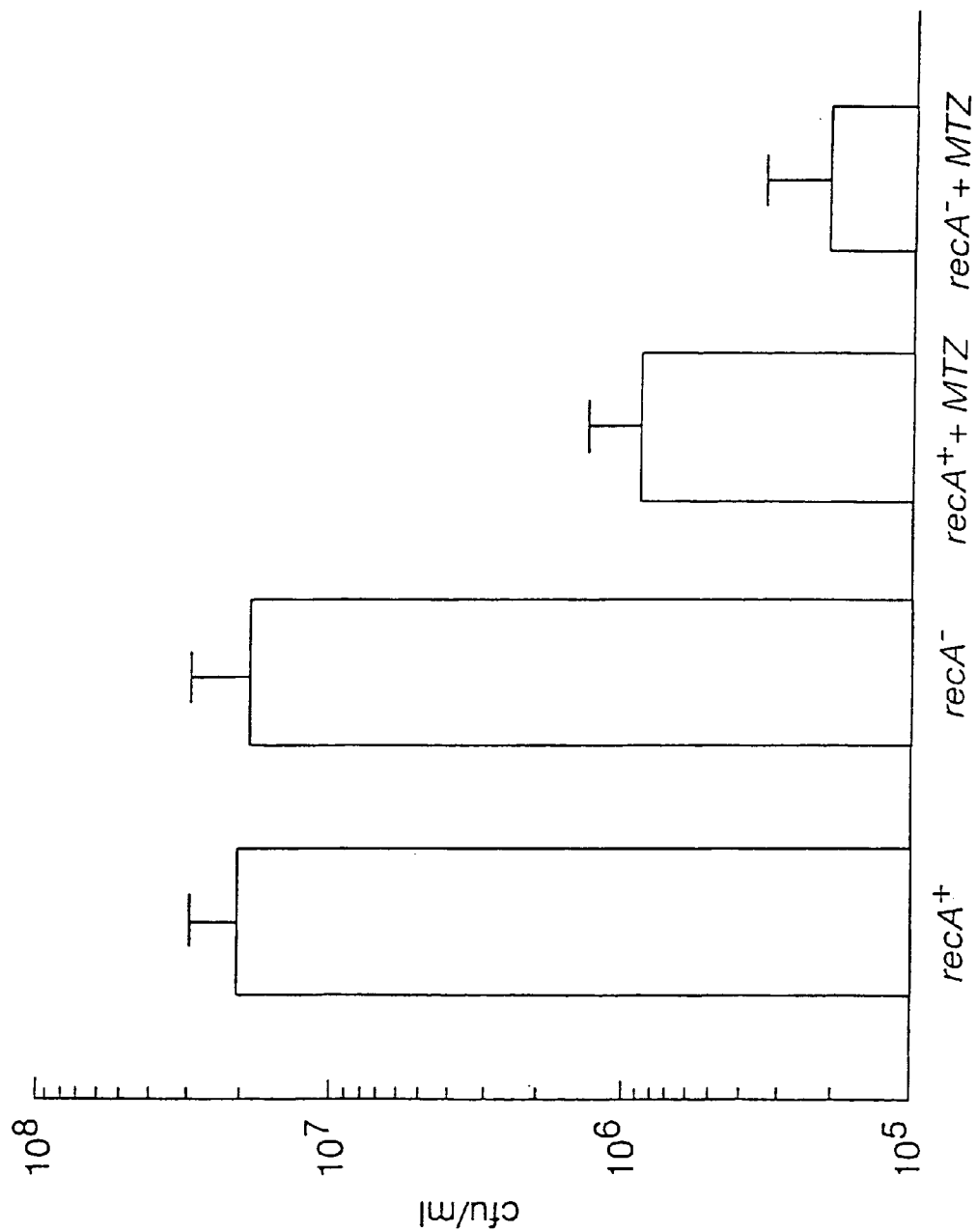

FIG. 4 shows survival under dormancy conditions. Survival of parental M. bovis BCG and the recA knock-out mutant under dormancy culture conditions was investigated by determining the numbers of cfu after 20 days of incubation in the presence or absence of metronidazole (10 μg/ml).

Figure 5:
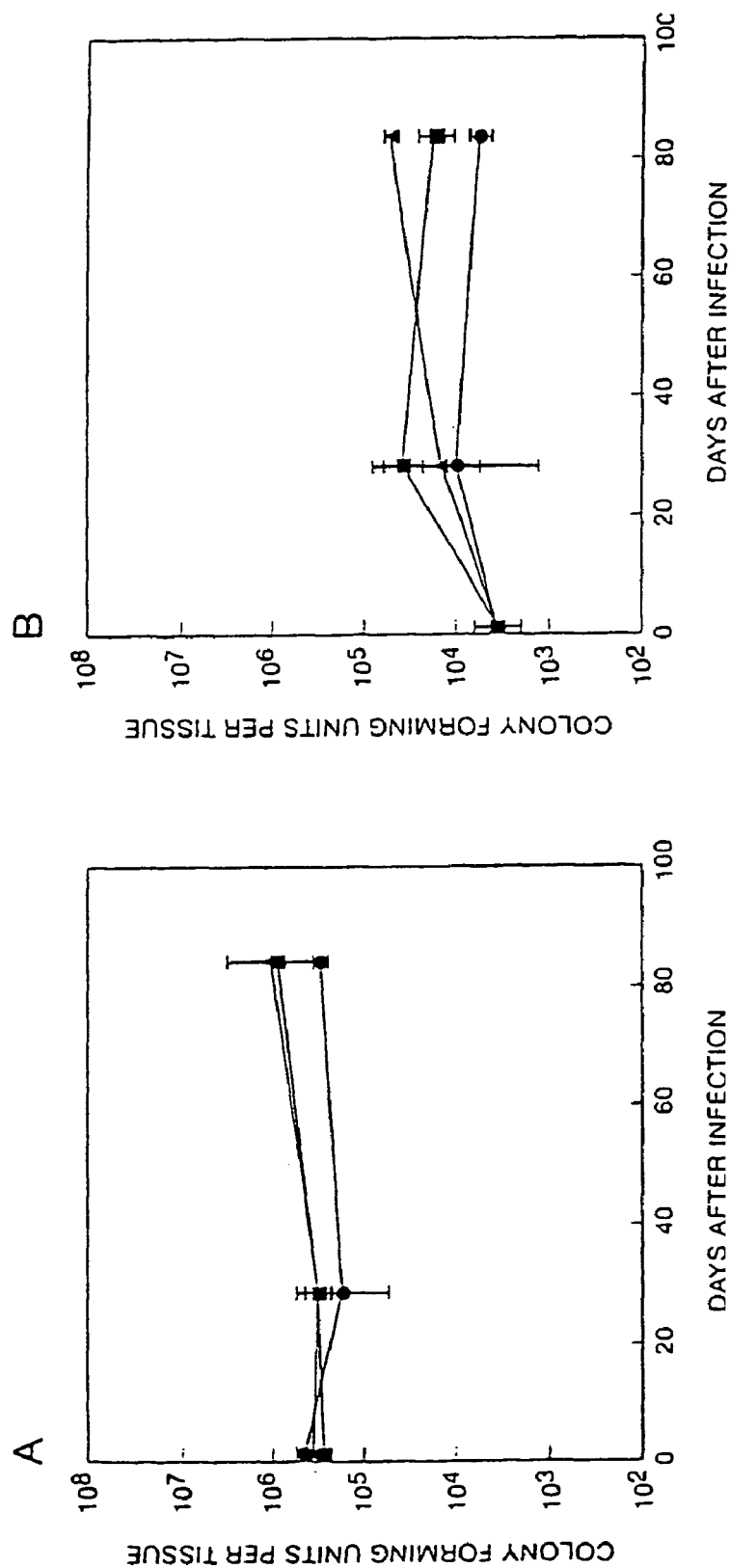

FIG. 5 shows the course of infection in Balb/c mice. Parental M. bovis BCG (●), a recA single cross-over transformant (■) and a recA knock-out mutant (▲) were injected into the tail vene (approx. $10^6$ cfu/animal). The number of bacteria in spleen (A) or lung (B) were determined at different time points.

Figure 6:
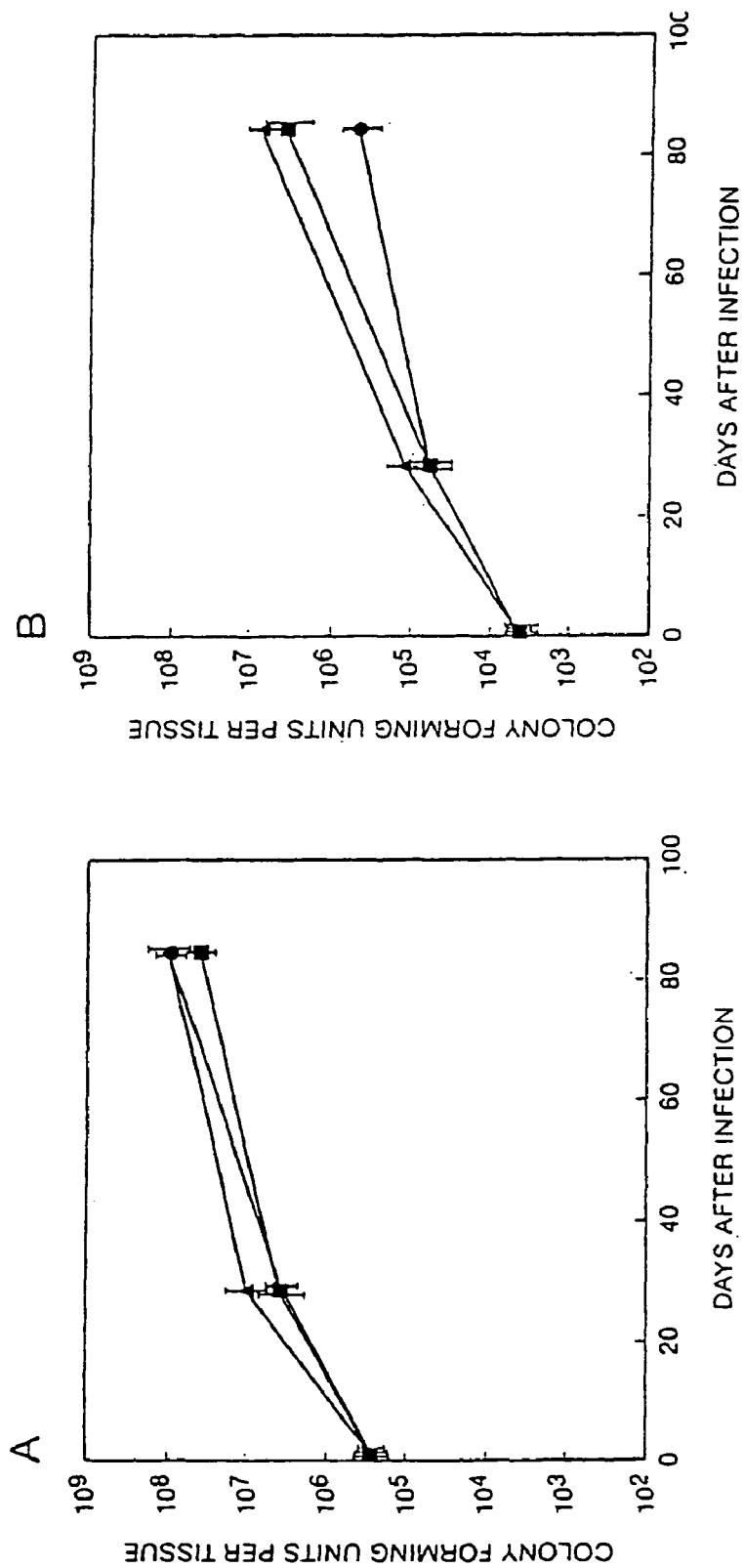

FIG. 6 shows the course of infection in nude mice. Parental M. bovis BCG (●), a recA single cross-over transrormant (■) and a recA knock-out mutant (▲) were injected into the tail vene (approx. $10^6$ cfu/animal). The number of bacteria in spleen (A) or lung (B) were determined at different time points.

EXPERIMENTAL

Mutants of M. tuberculosis have previously been generated using transposon mutagenesis (Camacho, L. R. et al. (1999) Mol. Microbiol. 34: 257–267; Cox, J. S. (1999) Nature 402: 79–83). However, the distribution of IS-elements in the M. tuberculosis genome is not random (Gordon, S. V. et al (1999) Microbiology 145: 881–892) and it is difficult to target genes which are small in size.

Despite major efforts in mycobacterial genetics during the past years, targeted gene inactivation in M. tuberculosis complex remains a technical hurdle. Due to the moderate transformation efficiencies and poor frequencies of double cross-over recombination, the generation of knock-out mutants is laborious and often requires the screening of numerous transformants (Yuan, Y. et al (1998) Proc. Natl. Acad. Sci. USA 95: 9578–9583).

The use of dominant negative selectable markers has proven a valuable tool for targeted gene inactivation in some mycobacteria (Sander, P. et al (1995) Mol. Microbiol. 16: 991–1000; Pelicic, V. et al (1996) J. Bacteriol. 178: 1197–1199; Pavelka, M. S., and Jacobs, W. R. (1999) J. Bacteriol. 181: 4780–4789; Pelicic, V. et al (1997) Proc. Natl. Acad. Sci. USA 94: 10955–10960). rpsL was the first counterselectable marker introduced into mycobacterial genetics (Sander et al., 1995 supra). This marker has been used as dominant negative selectable marker in Mycobacterium smegmatis, as the rpsL wild-type gene confers a streptomycin sensitive phenotype when transformed into a streptomycin resistant strain with a mutant rpsL (Sander et al., 1995 supra, Sander, P et al (1996) Mol. Microbiol. 22: 841–848; Frischkorn et al., 1998 supra).

However, the technique has not been previously applied to mycobacteria of the M. tuberculosis complex such as M. bovis or M. tuberculosis. Various modifications were made to the technique by the present inventors in order to generate M. tuberculosis or M. bovis BCG mutants.

Materials and Methods

DNA Manipulations, Isolation of Plasmids

Standard techniques were used for DNA manipulation. All initial cloning procedures were performed in E. coli XL1-Blue MRF. Plasmids were prepared with a Quiagen plasmid preparation kit according to the manufacturer's recommendations. Plasmid DNA was dissolved in TE-buffer in concentrations of 500–1000 ng/μl.

Cultivation of Mycobacteria

When cultivated on solid medium M. bovis BCG strain Pasteur (ATCC 35734) was grown on Middlebrook 7H10 agar supplemented with oleic acid albumin dextrose (OADC) (Difco) for 3–4 weeks. Tween 80 was added to liquid broth 7H9-OADC to avoid clumping; incubation was performed in a roller bottle for 10–20 days. Antibiotics were added to the following concentrations: kanamycin 25 μg/ml; hygromycin 50 μg/ml; streptomycin 25 μg/ml.

Generation of Suicide Vectors

For the generation of suicide vectors precA::aph-rpsL and precA::hyg-rpsL the following cloning steps were performed: a 5.2 kb ApaI fragment from plasmid pEJ126 (Davis et al., 1991 supra) containing M. tuberculosis recA was subcloned into the PstI site of plasmid pbluescript KSII⁻ (Stratagene) resulting in plasmid pBluescript-recA. From this vector a 1.3 kbp internal PstI fragment was substituted by a 1.3 kbp aph-cassette isolated as a PstI fragment from plasmid pUC4K (Pharmacia) or by a 1.8 kbp hyg-cassette isolated as a BglII-fragment from plasmid pIJ963 (Lydiate, D. J. et al (1989) *J. Gen. Microbiol*. 135: 941–955) resulting in plasmids precA::aph and precA::hyg, respectively. From these vectors fragments comprising the inactivated recA gene were removed by digestion with EcoRV and SpeI and cloned into ptrpA-1-rpsL previously digested with SacI, blunt-ended and subsequently digested with SpeI (Sander et al., 1995 supra), resulting in suicide vectors precA::aph-rpsL and precA::hyg-rpsL, respectively. The cloning procedures were confirmed by DNA sequencing.

Southern Blot Analyses

For Southern blot analyses 200–500 ng of genomic DNA were digested with an appropriate restriction enzyme. Fragments were separated on an agarose gel and treated according to standard protocols with HCl, NaOH and neutralization buffer. DNA was transferred to a Hybond-N™ membrane (Amersham) with a vacuum blotting apparatus and cross-linked by UV irradiation. DNA was hybridized to recA probe (a 1.6 kbp ApaI/PstI fragment from pBluescript-recA) labeled with digoxygenin according to the manufacturer's instructions (Boehringer. Mannheim), washed under stringent conditions and developed with an antibody directed against digoxigenin coupled with horse radish peroxidase.

Western Blot Analyses

M. bovis BCG strains were grown in 100 ml of Dubos broth, induced with ofloxacin (1 μg/ml) for 24 h and cell free extracts were prepared as described previously (Papavinasasundaram, K. G. et al (1997) *Mol. Microbiol* 24: 141–153). Cell-free extracts corresponding to 30 μg of protein, as determined by BCA protein kit (Pierce), were separated by SDS-polyacrylamide electrophoresis through a 10% polyacrylamide gel and the proteins were electroblotted onto a PVDF membrane (Immobilon-P, Millipore). The membrane was blocked with 10% non-fat milk in TTBS [20 mM Tris (pH7.5), 0.5 M NaCl buffer containing 0.1% Tween 20] and incubated with 1:1000 dilution of a mouse antiserum raised against purified M. tuberculosis RecA protein. Mice antibody conjugated to horseradish peroxidase (Dako) was used as secondary antibody. After washing with TTBS, the blot was developed with diaminobenzidine reagent solution as described previously (Davis, E. O. et al (1992) *Cell* 71: 201–210).

Generation of M. bovis BCG SMR1

M. bovis BCG (strain Pasteur) was grown in liquid medium until an optical density of approx. 1.0. Cells were collected and spread on 7H10-OADC agar containing streptomycin at a concentration of 20 μg/ml. After 4 weeks of incubation at 37° C. single colonies were picked and re-streaked on 7H10-OADC agar containing streptomycin to confirm the streptomycin resistant phenotype. The genotype of the streptomycin resistant strains was determined by PCR mediated amplification of rrs and rpsL. Sequencing of rrs and rpsL PCR products revealed a single A to G transition in rpsL codon 88 conferring an amino acid exchange from lysine to arginine.

Transformation of M. bovis BCG SMR1

*M. bovis* BCG SMR1 was grown in a 2 l roller bottle containing 400 ml 7H9-OADC-Tween until an OD of 0.6 was achieved. One day before harvesting the cells glycine was added to a final concentration of 1.5% (v/v) and cells were incubated for an additional 24 hours. All following steps were performed at room temperature. Cells were harvested by centrifugation, washed several times with 10% glycerol and finally resuspended in a volume of 5 ml. For electroporation 400 μl competent cells were mixed with 1 μg supercoiled plasmid DNA and electroporated in a BioRad Gene pulser II with the following settings: 2.5 kV, 1000 Ohms, 25 μF. After electroporation cells were resuspended in 4 ml of 7H9-OADC-Tween and incubated for 20 h with vigorous shaking at 37° C. Following incubation appropriate dilutions were plated on selective agar. Single colonies were picked, restreaked and grown in liquid broth when necessary.

Transformants which had undergone a homologous single cross-over were grown in liquid broth until an optical density of approximately 0.5 was achieved. Afterwards, appropriate dilutions were spread on plates containing either kanamycin, hygromycin, kanamycin plus streptomycin, or hygromycin plus streptomycin. After 4 weeks of incubation at 37° C. the efficiency of counterselection was determined by dividing the number of colonies obtained on plates containing kanamycin plus streptomycin or hygromycin plus streptomycin by the number of colonies obtained on kanamycin or hygromycin, respectively.

Construction of RecA$^-$ *M. tuberculosis*

The suicide vector precA::hyg-rpsL was introduced into *M. tuberculosis* 1424, a streptomycin resistant strain of *M. tuberculosis* H37Rv containing a point mutation in the rpsL gene (K42R), by electroporation and plated on 7H11 agar containing 50 μg $ml^{-1}$ hygromycin. Transformants which had undergone a homologous single crossover were identified by Southern analysis, grown in liquid broth to OD~0.5, and dilutions were plated on 7H11+hygromycin (50 μg $ml^{-1}$)+streptomycin (100 μg $ml^{-1}$). Colonies obtained from these counterselection plates were tested by Southern analysis to identify those that arose by a second crossover event. Standard blotting procedures were used (Sambrook et al., 1989 supra) and DNA was hybridised to a 1.6 kb ApaI/PscI fragment of pBluescript-recA (5' recA probe) using the digoxygenin system according to the manufacturer's instructions (Boehringer, Mannheim).

Phenotypic Characterization

EMS/MMS Assay

7H9-OADC medium containing EMS or MMS was inoculated with 1/50 th volume of a freshly grown culture (OD 0.5). After 6 days of incubation at 37° C. the optical density was determined. 7H9-OADC medium without alkylating chemicals served as a control.

UV Irradiation Assay

For the UV-irradiation assay, 100 μl aliquots of a freshly grown culture ($OD_{600}$=0.1) were placed in an inverted lid of a 24 well culture plate and put under a standard germicidal UV lamp (distance 20 cm). Cells were irradiated for different time periods and samples were removed and plated on 7H10-OADC. Mean values and standard deviations are shown from three independent experiments. Appropriate dilutions of each culture were plated out in duplicate.

In-vitro Induced Dormancy

Experiments were performed as described previously using an in vitro dormancy model (Lim, A. et al (1999) *J.*

*Bacteriol.* 181: 2252–2256). Briefly, screw-cap test tubes (20 mm by 125 mm) with a total fluid capacity of 25.5 ml were used. An early log phase culture was diluted to an $OD_{600}$ of 0.005 in a total volume of 17 ml Dubos broth (Difco). Solid caps with latex liners were tightly screwed down (limited oxygen supply) and the cultures were gently stirred at 170 rpm for 20 days. Self-generated oxygen depletion was monitored via the decolorisation of the oxygen indicator dye, methylene blue. Growth of cultures was monitored by $OD_{600}$; viable counts were determined by plating appropriate dilutions on Dubos oleic album agar (Difco). When indicated metronidazole was added at a concentration of 10 μg/ml. Mean values and standard deviations were determined from three independent experiments. Each experiment was carried out with duplicate cultures. Appropriate dilutions of each culture were plated out in triplicates.

Infections

Balb/c mice (6–8 weeks old) were obtained from the breeding facility at the National Institute for Medical Research, Mill Hill. *M. bovis* BCG strains were grown in Dubos broth. Logarithmically growing cultures were diluted in saline to an OD of 0.8; 0.2 ml (approximately $10^6$ cfu) were injected into the tail vein. Mice were sacrificed according to ethical guidelines at the times indicated (three mice per BCG strain for each time point), the spleen and lungs were removed, weighed and homogenized. The suspensions were serially diluted in saline and then plated on 7H10 agar supplemented with OADC. The plates were incubated at 37° C. for 3 weeks. The results were calculated and expressed as cfu per organ.

The strain *M. bovis* BCG SMR1 (for list of strains and plasmids see Table 1) is a streptomycin resistant derivative of *M. bovis* BCG; this strain has a mutation in rpsL codon 88 Lys to Arg, a mutation known to confer a streptomycin resistant phenotype (Finken et al., 1993 supra).

Transformation experiments were performed with plasmid pMV361 (Stover et al., 1991 supra) and pMV361-rpsL (Sander et al., 1995 supra) to investigate whether the cloned rpsL wild-type gene was expressed functionally in BCG and to verify that streptomycin resistance in BCG SMR1 is not due to additional mutations,; pMV361-rpsL carries the *M. tuberculosis* wild-type rpsL gene under control of its own promoter.

Transformation efficiencies were in the range of $10^4$ to $2\times10^4$ for both vectors when transformants were selected on medium containing kanamycin, the positive selection marker provided by pMV361. In the presence of kanamycin plus streptomycin the number of colonies obtained withvector pMV361-rpsL was reduced $10^4$-fold, whereas the number of transformants obtained with vector pMV361 was not affected.

Transformation and Genetic Characterization

Transformation of *M. bovis* BCG SMR1

*M. bovis* BCG SMR1 was transformed with suicide vectors precA::aph-rpsL and precA::hyg-rpsL, respectively. These vectors carry a *M. tuberculosis* recA fragment from which part of the coding region and part of the intein coding region have been substituted by either a kanamycin or a hygromycin resistance cassette. These vectors do not contain a mycobacterial origin of replication and thus are unable to replicate in *M. tuberculosis* complex. The wild-type rpsL gene flanking the inactivated target gene is used as counterselectable marker.

After electroporation, transformants were selected on medium containing either kanamycin or hygromycin. Transformation efficiencies when using a suicide vector in *M. tuberculosis* complex are in the range of 10–50 transformants per μg plasmid DNA. Eleven kanamycin resistant and four hygromycin resistant transformants were chosen at random for further investigations.

Genetic Analysis of Transformants and Counterselection

Of the eleven kanamycin resistant clones investigated, nine clones contained the aph cassette indicating that these colonies arose from transformation with the suicide vector rather than representing spontaneous kanamycin resistant mutants. Genomic DNAs were isolated form these as well as the four hygromycin resistant transformants and investigated by Southern blot analyses using a recA fragment as probe.

Two of the nine kanamycin resistant transformants revealed a pattern indicating a 5' single cross-over at the recA locus. After digestion with SmaI the parental wild-type strain showed a single 2 kbp fragment. Two transformants showed a 2.6 kbp and a 4.9 kbp fragment, respectively; these fragments represent the vector derived, inactivated recA and the chromosomally encoded functional recA gene. Note that the probe used did not allow to distinguish whether the remaining transformants resulted from a single cross-over in the 3'-flanking region or from illegitimate recombination. Three of the four hygromycin resistant transformants showed a pattern indicative of a 5' single cross-over. Two kanamycin and two hygromycin resistant transformants for which a homologous single cross-over was demonstrated were grown up in liquid broth and subjected to counterselection on medium containing kanamycin plus streptomycin or hygromycin plus streptomycin, respectively. Transformants with a kanamycin plus streptomycin resistant phenotype arose with a frequency of $10^{-4}$ to $10^{-5}$. Hygromycin plus streptomycin resistant transformants were observed with a similar frequency.

Transformants were screened for the absence of the deleted recA/intein coding sequence by PCR; seven of 40 transformants showed a PCR result indicating recA inactivation. Transformants with a recA deletion were grown up, and investigated by Southern blot analysis. Following digestion with SmaI, the kanamycin/streptomycin resistant transformants revealed a single 2.6 kbp fragment; the absence of the 2 kbp and the 4.9 kbp gene fragments and the presence of a single 2.6 kbp fragment indicates a second cross-over event resulting in loss of the functional recA copy. The genotype was confirmed by further genetic analyses. The hygromycin/streptomycin resistant transformants showed a single fragment of 3.3 kbp indicative of a recA inactivation.

For the further investigations one of the kanamycin inactivated recA mutants was chosen.

Western Blot Analysis

Western blot analyses using an anti-serum raised against *M. tuberculosis* RecA was performed with the parental strain, a single cross-over transformant and the corresponding knock-out mutant. Approximately 30 μg. protein was separated on a polyacrylamide gel, transferred to a PVDF membrane, and probed with an antibody raised against *M. tuberculosis* RecA. A single band of approx. 40 kDa corresponding to the mature, spliced form of *M. tuberculosis* RecA was observed in extracts of both the parental strain and the single cross-over transformant but not in the $recA^-$ mutant selected on kanamycin plus streptomycin, indicating absence of the RecA protein and thus confirming the data obtained by Southern blot analysis.

In-vitro Characterization of *M. bovis* BCG recA

*M. bovis* BCG recA⁻ Strains are Sensitive Towards Alkylating Agents

One of the most noticeable phenotypes of recA$^-$ strains is their increased sensitivity towards DNA damaging agents (Kowalczykowski, S. C. et al (1994) *Microbiol. Rev.* 58: 401–465). To investigate the physiological effects of recA inactivation, several tests with different DNA damaging agents were performed. The ability of recA$^+$ and recA$^-$ strains to grow in the presence of ethylmethane sulfonic ethyl ester (EMS) or ethylmethane sulfonic methyl ester (MMS) was determined in liquid broth (Table 2).

The presence of 0.05% EMS only slightly inhibited growth of the recA$^+$ strain. In contrast, growth of the recA$^-$ strain was reduced 10-fold compared to that of the control. Similar results were obtained with MMS. At a concentration of 0.006% MMS growth of the recap strain was not significantly affected, whereas growth of the recA strain was inhibited by approx. 90%. In the absence of DNA alkylating agents the growth rate of the recA$^+$ and the recA$^-$ strain were indistinguishable. The single cross-over transformant essentially behaved like the recA$^+$ strain in the presence of DNA damaging agents.

*M. bovis* BCG recA$^-$ Mutants are Sensitive to UV-irradiation

Irradiation with UV light is frequently used to compare the effectiveness of DNA repair mechanisms. Inactivation of the recA gene rendered *M. bovis* BCG sensitive to UV irradiation: the recA strain exhibited a 10,000 fold decreased viability after 30 s of irradiation compared with a 25-fold decrease for the recA$^+$ strain (FIG. 2). The survival rate decreased dramatically at higher irradiation dosages; only very few survivors of the mutant strain were detected after 60 s of irradiation (<0.0001%), compared to about 0.01% survival rate of the parental strain. These results support previous observations that—despite the presence of an intein—*M. bovis* BCG RecA is functionally expressed and promotes DNA repair mechanisms in mycobacteria (Frischkorn, K. et al (1998) *Mol. Microbiol*. 29:1203–1214; Papavinasasundaram et al., 1998 supra).

In-vitro Induced Dormancy and Metronidazole Resistance

The obligate aerobe *M. tuberculosis* complex can enter an anerobic dormant state in which it survives for extended periods of time (for review: Wayne, L. G. (1994). *Eur. J. Microbiol. Infect. Dis*. 13: 908–914). We investigated recA$^+$ and recA$^-$ strains with respect to their ability to survive in an in-vitro dormancy model (Wayne, L. G. and Hayes, L. G. (1996) *Infect. Immun*. 64: 2062–2069) to determine whether the dormancy response is affected by a loss of recA function. Mycobacteria were grown in sealed and stirred tubes to achieve self-generated oxygen depletion, a signal which triggers entry into the dormant state. Growth of the cultures was followed by measuring the optical density; the number of cells surviving oxygen depletion was determined by plating. Self-generated oxygen depletion was judged by fading/decolorization of the indicator methylene blue.

With respect to optical density recA$^+$ and recA$^-$ strains behaved identically (FIG. 3). A plateau was achieved after approx. 8 days. After day 9 and after day 15, respectively, fading and decolorization of the oxygen indicator methylene blue was observed in each of the cultures. After incubation for an additional 5 days cultures were harvested and the number of cfu's was determined (FIG. 4). The recA genotype did not affect the number of viable cells after oxygen depletion indicating that RecA does not affect the in-vitro induced dormancy survival.

Metronidazole is the first lead compound active against dormant *M. tuberculosis*. Metronidazole does not affect the growth of aerobic grown cultures but acts exclusively on anaerobic grown *M. tuberculosis* complex (Wayne, L. G., and Sramek, H. A. (1994). *Agents Chemother*. 38: 2054–2058).

Compared to recA$^{30}$ *M. bovis* BCG, BCG, recA mutant showed increased susceptibility to metronidazole, i.e. the number of viable cells was reduced about 20-fold by metronidazole for the recA$^-$ strain, but a 100-fold reduction in the number of viable cells was observed in the recA$^-$ mutant (FIG. 4).

Survival of the *M. bovis* BCG recA Mutant in Mice

DNA repair mechanisms in general and recA in particular are important virulence factors for the survival of intracellular pathogens, such as *Salmonella* (Buchmeier, N. A. et al. (1993). *Mol. Microbiol*. 7: 933–936). Although wild-type *M. bovis* BCG does not cause a progressive infection in mice it does persist in tissue for a significant period of time.

Balb/C mice were infected by i.v. injection with *M. bovis* BCG recA$^+$, the single cross-over transformant and the recA$^-$ strain. After days 1, 28, and 84, organs (spleen and lung) were removed, homogenized, and appropriate dilutions plated on 7H10 agar. The plates were incubated for 3 weeks and the number of cfu per organ were calculated. As shown in FIG. 5 the knock-out mutant showed no difference in the course of infection compared to the wild-type strain, neither in the spleen nor in the lung of infected Balb/c mice. These data indicate that RecA is not essential for survival in the high dose mouse infection model. We also compared growth of the three strains in athymic mice and again there was no significant difference in growth in lungs or spleen.

Genetic Stability

A recombination assay selecting for drug resistance was used to demonstrate that homologous recombination is eliminated in RecA$^-$ *M. smegmatis.*

*M. smegmatis* recA$^+$ and *M. smegmatis* recA$^-$ were transformed with replicating vectors (derivatives of pMV261) carrying a non-functional fragment of rpoB using conventional procedures (Sander et al., 1995 supra). The rpoB fragment either carried a wild-type sequence or a mutation conferring rifampicin resistance.

Upon recombination of the (mutated) fragment with the chromosomally encoded rpoB gene (RNA polymerase β subunit) the mutant fragment is incorporated into the functional gene and confers rifampicin resistance, while the wild-type fragment should not confer any selectable phenotype (control).

The results shown in Table 3 indicated that the generation of the resistant phenotype was RecA dependent. Homologous recombination in mycobacteria therefore requires the functional RecA gene product.

Discussion

The approach described herein to transform *M. tuberculosis* cells was similar to a strategy which has previously been used successfully to generate allelic exchange mutants in *M. smegmatis* (Sander et al., 1995 supra). However, as transformation efficiencies are a critical issue, the original procedure was modified to a two-step allelic exchange incorporating successive steps of positive and negative selection instead of a one-step double selection. This modified approach overcomes reported problems with unfavourable ratios of single cross-over transformants versus double cross-over transformants (i.e. allelic replacement) in *M. tuberculosis*. (Yuan et al., 1998 supra).

RecA is a multifunctional and ubiquitous protein involved both in general recombination and in DNA repair. As an inducer of the SOS response, RecA regulates at least 20 genes, most of which are usually suppressed by LexA (Miller, R. V., and Kokjohn, T. A. (1990) *Annu. Rev. Microbiol.* 44: 365–394). Mycobacteria possess the key elements of a functional SOS-system, with a LexA protein binding to a consensus sequence GAACnnnnGTTC (Movahedzadeh, F. et al (1997) *J. Bacteriol.* 179: 3509–3518; Durbach, S. I. et al (1997) *Mol. Microbiol.* 26: 643–653).

Investigations on *M. tuberculosis* RecA function have previously been performed in vitro, in *E. coil* or in *M. smegmatis* (Davis et al., 1991, 1992 supra; Davis, E. O. et al (1994) *EMBO J.* 13: 699–703; Kumar, R. A. et al (1996) *Biochem*: 35: 1793–1802; Frischkorn et al., 1998 supra; Papavinasasundaram et al., 1998 supra; Vaze, M. B., and Muniyappa, K. (1999) Biochem. 38: 3175–3186). These investigations demonstrated that the mature *M. tuberculosis* RecA promotes DNA repair mechanisms and homologous recombination (Frischkorn et al., 1998 supra; Papavinasasundaram et al., 1998 supra). However, a different, homologous gene, e.g. radA (corresponding to H37Rv open reading frame Rv 3585, Cole, S. T. et al (1998) *Nature* 393: 537–544) may compensate for RecA function in vivo. The present investigations provide an indication that *M. bovis* BCG has a non-redundant recA gene, which is essential to promote DNA repair mechanisms.

It has recently been demonstrated that *M. bovis* BCG (Lim et al., 1999 supra) and *M. tuberculosis* are able to enter a dormant state. This response is triggered by slow self-generated depletion of oxygen (Wayne, 1994 supra) Entry into the dormant state is an adaptive process as sudden oxygen depletion results in cell death (Wayne, L. G., and Diaz, G. A. (1967) *J. Bacteriol.* 93: 1374–1381). Although some genes which have increased expression in the dormant phase, have been identified e.g. α-crystallin like protein [Yuan, Y. et al (1996) *J. Bacteriol.* 178: 4484–4492] and glycin-dehydrogenase [Wayne, L. G. and Lin, K. Y. (1982). *Infect. Immun.* 37: 1042–1049]), little is known concerning the factors involved in survival during dormancy.

Experiments in an in-vitro dormancy model are described herein. As the number of viable mycobacterial cells after oxygen depletion was essentially identical for the recA+ and recA− strain, these experiments show that RecA does not play an essential role in entry, survival or exit from the dormant state.

Numerous reports have demonstrated that recA represents an important virulence factor: RecA is involved in stress survival (Duwat, P. et al (1995) *Mol Microbiol* 17: 1121–1131) mediates aerotolerance in microaerophilic bacteria (Cooper, A. J. et al (1997) *J. Bacteriol.* 179: 6221–6227), induces production of colicins, pyocins (Miller and Kokjohn, 1990 supra), and extracellular degradative enzymes (Liu, Y. et al (1996) *Mol. Microbiol.* 22: 909–918), mediates amplification of toxin genes (Goldberg, I., and Mekalanos, J. J. (1986) *J. Bacteriol.* 165: 723–731). Most notably, *Salmonella* recA− strains are highly attenuated, both in cultured macrophage cells (Buchmeier et al., 1993 supra) and in a mouse infection model (Buchmeier et al., 1995 supra). This effect has been attributed to the DNA damaging effect of the oxidative burst and the reduced ability of the mutants to perform DNA repair (Storz et al., 1990 supra).

Our results unexpectedly show that RecA does not contribute to the establishment and maintenance of infection in *M. bovis* BCG or *M. tuberculosis*. This is an important finding since persistence of BCG following vaccination is thought to be a significant contributory factor to its immunogenicity; a mutant BCG which is rapidly eliminated would not be an effective vaccine.

Vaccines are the most cost-effective intervention known to prevent disease. Viable carrier systems in general and *M. tuberculosis* complex mycobacteria such as *M. bovis* BCG in particular offer great potential for innovative approaches for development of polyvalent vaccines (Matsuo et al., 1990 supra; Winter et al., 1991 supra; Aldovini and Young, 1991 supra; Stover et al., 1991 supra). BCG is the most widely used vaccine: it can be given as a single dose at birth, and can confer long lasting immunity. RecA mutants may be a valuable tool for further development of *M. bovis* BCG as an antigen delivery system for expression of foreign antigens.

TABLE 1

Strains and vectors used

| | |
|---|---|
| Strains | |
| *E. coli* XL1-Blue | Stratagene |
| *M. bovis* BCG strain Pasteur | ATCC 35734 |
| *M. bovis* BCG SMR1. | this study |
| *M. bovis* BCG recA*/recA::aph | this study |
| *M. bovis* BCG recA*/recA::hyg | this study |
| *M. bovis* BCG recA::aph | this study |
| *M. bovis* BCG recA::hyg | this study |
| Plasmids | |
| pMV361 | Stover et al., 1991 |
| pMV361-rpsL | Sander et al., 1995 |
| pEJ126 | Davis et al., 1991 |
| pUC4K | Pharmacia |
| pIJ963 | Lydiate et al., 1989 |
| pBluescript SKII- (Stratagene) | *E. coli* cloning vector |
| ptrpA-1-rpsL | Sander et al., 1995 |
| pBluescript-recA | This study |
| pBluescript-recA::aph | This study |
| pBluescript-recA::hyg | This study |
| precA::aph-rpsL | This study |
| precA::hyg-rpsL | This study |

TABLE 2

Growth in the presence of alkylating agents

| | $recA^+$ | $recA^+/recA^-$ | $recA^-$ |
|---|---|---|---|
| 7H9 | 0.687 | 0.653 | 0.679 |
| + EMS (0.05%) | 0.374 | 0.376 | 0.077 |
| + MMS (0.006%) | 577 | 0.608 | 0.098 |

Growth as determined by optical density (OD600 nm) of parental $recA^+$, single cross-over transformant ($recA^+/recA^-$) and $recA^-$ mutant in 7H9-OADC medium containing EMS [0.05% (v/v)] or MMS [0.006% (v/v)]. Cultures were inoculated with approximately $10^6$ cfu/ml and incubated for 6 days.

TABLE 3

Frequencies of mutation to rifampicin resistance by recombination

| Strain | plasmid | mean relative frequency[c] |
|---|---|---|
| *M. smegmatis* $recA^+$ | rpoBwt[a] | 1.0 |
| *M. smegmatis* $recA^+$ | rpoBmut[b] | 145.0 |

TABLE 3-continued Frequencies of mutation to rifampicin resistance by recombination

| Strain | plasmid | mean relative frequency[c] |
|---|---|---|
| M. smegmatis recA⁻ | rpoBwt | 0.8 |
| M. smegmatis recA⁻ | rpoBmut | 0.9 |

[a]wt = wild type rpoB fragment
[b]mut = mutated rpoB fragment
[c]relative to the background; spontaneous frequency of mutation to rifampicin resistance

The invention claimed is:

1. A *mycobacterium* which is a member of the *M. tuberculosis* complex and which has an inactivated recA function.

2. A *mycobacterium* according to claim 1 which is *Mycobacterium bovis* BCG or *Mycobacterium tuberculosis*.

3. A *mycobacterium* according to claim 1 which is non-virulent.

4. A *mycobacterium* according to claim 1 wherein the recA gene of said cell is inactivated by mutation.

5. A *mycobacterium* according to claim 1 which comprises genetic material encoding an antigen or immunogen exogenous or foreign to the *mycobacterium*.

6. A *mycobacterium* according to claim 5 wherein said antigen is a viral, protozoal, tumour cell, bacterial or fungal antigen.

7. A *mycobacterium* according to claim 1 for use in a method of treatment of the human or animal body.

8. A method for improving the genetic stability of a *M. tuberculosis* complex cell without affecting the persistence of the cell in a host, comprising inactivating the recA gene within the cell.

9. A method according to claim 8 comprising replacing the endogenous recA gene of said cell with a recA transgene which carries a mutation which reduces the function of the recA transgene.

10. A method according to claim 8 comprising formulating said cell into a pharmaceutical preparation.

11. A pharmaceutical composition comprising the *mycobacterium* according to claim 1.

12. A method of making a pharmaceutical composition comprising admixing the *mycobacterium* according to claim 1 with a pharmaceutically acceptable excipient, vehicle or carrier.

13. A method comprising the administration of the *mycobacterium* according to claim 1 to a mammal in need thereof for use in the treatment of a disorder in which an immune response against the cell is beneficial.

14. A method according to claim 13 wherein the disorder is a mycobacterial infection.

* * * * *